(12) United States Patent
Weitz et al.

(10) Patent No.: US 11,607,658 B2
(45) Date of Patent: Mar. 21, 2023

(54) FORMATION OF COLLOIDS OR GELS WITHIN DROPLETS

(71) Applicants: President and Fellows of Harvard College, Cambridge, MA (US); Massachusetts Eye and Ear Infirmary, Boston, MA (US)

(72) Inventors: David A. Weitz, Bolton, MA (US); Huidan Zhang, Cambridge, MA (US); Nai Wen Cui, Cambridge, MA (US); Fengyang Lei, Cambridge, MA (US); Eleftherios Paschalis Ilios, Hingham, MA (US)

(73) Assignees: President and Fellows of Harvard College, Cambridge, MA (US); Massachusetts Eye and Ear Infirmary, Boston, MA (US)

( * ) Notice: Subject to any disclaimer, the term of this patent is extended or adjusted under 35 U.S.C. 154(b) by 1113 days.

(21) Appl. No.: 16/315,245

(22) PCT Filed: Jul. 7, 2017

(86) PCT No.: PCT/US2017/041053
§ 371 (c)(1),
(2) Date: Jan. 4, 2019

(87) PCT Pub. No.: WO2018/009766
PCT Pub. Date: Jan. 11, 2018

(65) Prior Publication Data
US 2019/0160445 A1 May 30, 2019

Related U.S. Application Data
(60) Provisional application No. 62/360,143, filed on Jul. 8, 2016.

(51) Int. Cl.
*B01J 13/00* (2006.01)
*B01J 2/08* (2006.01)
*B01L 3/00* (2006.01)

(52) U.S. Cl.
CPC ............ *B01J 13/0052* (2013.01); *B01J 2/08* (2013.01); *B01L 3/502715* (2013.01); *B01L 3/502784* (2013.01); *B01L 2200/027* (2013.01)

(58) Field of Classification Search
None
See application file for complete search history.

(56) References Cited

U.S. PATENT DOCUMENTS

| 5,512,131 A | 4/1996 | Kumar et al. |
| 6,355,198 B1 | 3/2002 | Kim et al. |
| (Continued) | | |

FOREIGN PATENT DOCUMENTS

| WO | WO 96/29629 | 9/1996 |
| WO | WO 01/89787 A2 | 11/2001 |
| (Continued) | | |

OTHER PUBLICATIONS

International Search Report and Written Opinion for Application No. PCT/US217/041053 dated Sep. 14, 2017.
(Continued)

*Primary Examiner* — J. Christopher Ball
(74) *Attorney, Agent, or Firm* — Wolf, Greenfield & Sacks, P.C.

(57) ABSTRACT

The present invention generally relates to microfluidic droplets and, including forming gels within microfluidic droplets. In some aspects, a fluid containing agarose or other gel precursors is transported into a microfluidic droplet, and caused to harden within the droplet, e.g., to form a gel particle contained within the microfluidic droplet. Surprisingly, a discrete gel particle may be formed even if the fluid
(Continued)

containing the agarose or other gel precursor, and the fluid contained within the microfluidic droplet, are substantially immiscible. Other aspects of the present invention are generally directed to techniques for making or using such gels within microfluidic droplets, kits containing such gels within microfluidic droplets, or the like.

24 Claims, 3 Drawing Sheets

(56) References Cited

U.S. PATENT DOCUMENTS

| | | | |
|---|---|---|---|
| 8,765,485 | B2 | 7/2014 | Link et al. |
| 9,757,698 | B2 | 9/2017 | Weitz et al. |
| 9,789,482 | B2 | 10/2017 | Link et al. |
| 9,878,325 | B2 | 1/2018 | Link et al. |
| 2005/0172476 | A1 | 8/2005 | Stone et al. |
| 2007/0003442 | A1 | 1/2007 | Link et al. |
| 2008/0014589 | A1 | 1/2008 | Link et al. |
| 2010/0136544 | A1 | 6/2010 | Agresti et al. |
| 2012/0132288 | A1 | 5/2012 | Weitz et al. |
| 2014/0305799 | A1 | 10/2014 | Link et al. |
| 2017/0246634 | A1 | 8/2017 | Weitz et al. |
| 2017/0354937 | A1 | 12/2017 | Weitz et al. |
| 2017/0361318 | A1 | 12/2017 | Link et al. |
| 2018/0117585 | A1 | 5/2018 | Link et al. |

FOREIGN PATENT DOCUMENTS

| | | | |
|---|---|---|---|
| WO | WO 2004/002627 | A2 | 1/2004 |
| WO | WO 2004/091763 | A2 | 10/2004 |
| WO | WO 2005/021151 | A1 | 3/2005 |
| WO | WO 2009/048532 | A2 | 4/2009 |
| WO | WO 2010/151776 | A2 | 12/2010 |
| WO | WO 2012/027366 | A2 | 3/2012 |
| WO | WO 2014/004630 | A8 | 1/2014 |
| WO | WO 2015/161223 | A1 | 10/2015 |
| WO | WO 2015/195698 | A1 | 12/2015 |
| WO | WO 2015/200616 | A1 | 12/2015 |

OTHER PUBLICATIONS

International Preliminary Report on Patentability for Application No. PCT/US217/041053 dated Jan. 17, 2019.
Lagus et al., A review of the theory, methods and recent applications of high-throughput single-cell droplet microfluidics. Journal of Physics D: Applied Physics. Feb. 22, 2013; 46(114005)1-21.
EP 17824957.9, Feb. 4, 2020, Extended European Search Report.
U.S. Appl. No. 15/829,371, filed Dec. 1, 2017, Link et al.
U.S. Appl. No. 15/659,307, filed Jul. 25, 2017, Weitz et al.
U.S. Appl. No. 15/320,408, filed Dec. 20, 2016, Weit et al.
PCT/US217/041053, Sep. 14, 2017, International Search Report and Written Opinion.
PCT/US217/041053, Jan. 17, 2019, International Preliminary Report on Patentability.
Extended European Search Report for Application No. EP 17824957 dated Feb. 4, 2020.
European Office Action dated Feb. 21, 2020 for Application No. EP 17824957.9.
European Office Action dated Feb. 18, 2021 for Application No. EP 17824957.9.

FORMATION OF COLLOIDS OR GELS WITHIN DROPLETS

RELATED APPLICATIONS

This application is a national stage filing under 35 U.S.C. § 371 of International Patent Application Serial No. PCT/US2017/041053, filed Jul. 7, 2017, entitled "Formation of Colloids or Gels Within Droplets," by Weitz, et al., which claims the benefit of U.S. Provisional Patent Application Ser. No. 62/360,143, filed Jul. 8, 2016, entitled "Formation of Colloids or Gels Within Droplets," by Weitz, et al., each of which is incorporated herein by reference in its entirety.

FIELD

The present invention generally relates to microfluidic droplets and, in particular, to forming gels within microfluidic droplets.

BACKGROUND

Hydrocolloids are hydrophilic polymers that contain many hydroxyl groups which may be polyelectrolytes. They are derived from vegetable, animal, microbial, or synthetic process and are naturally present in foodstuffs or added to control the functional properties of such materials. In most practical applications of hydrocolloids, they are primarily polysaccharides, although some proteins may be used. Hydrocolloids provide a renewable source of structuring and controlled release of agents for a variety of applications, and are commonly used in food, pharmaceutical, agricultural, and applications that require biocompatibility. Hydrocolloid gel networks are formed through entwining and cross-linking of polymer chains to generate three-dimensional network. Hydrocolloidal gels are useful in a variety of fields, and improvements in techniques to make such hydrocolloidal gels would be desirable.

SUMMARY

The present invention generally relates to microfluidic droplets and, including forming gels within microfluidic droplets. The subject matter of the present invention involves, in some cases, interrelated products, alternative solutions to a particular problem, and/or a plurality of different uses of one or more systems and/or articles.

In one aspect, the present invention is generally directed to a method comprising transporting a first fluid containing agarose at at least 0.5 vol % into a microfluidic droplet containing a second fluid, and causing the agarose gel to solidify to form a gel particle contained within the second fluid in the microfluidic droplet.

The method, in another aspect, is generally directed to inserting a first fluid containing a gel precursor at at least 0.5 vol % into a microfluidic droplet containing a second fluid, and causing the gel precursor to solidify to form a gel particle contained within the second fluid in the microfluidic droplet.

In another aspect, the present invention encompasses methods of making one or more of the embodiments described herein, for example, gel particles within microfluidic droplets. In still another aspect, the present invention encompasses methods of using one or more of the embodiments described herein, for example, gel particles within microfluidic droplets.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures.

DETAILED DESCRIPTION

The present invention generally relates to microfluidic droplets and, including forming gels within microfluidic droplets. In some aspects, a fluid containing agarose or other gel precursors is transported into a microfluidic droplet, and caused to harden within the droplet, e.g., to form a gel particle contained within the microfluidic droplet. Surprisingly, a discrete gel particle may be formed even if the fluid containing the agarose or other gel precursor, and the fluid contained within the microfluidic droplet, are substantially immiscible. Other aspects of the present invention are generally directed to techniques for making or using such gels within microfluidic droplets, kits containing such gels within microfluidic droplets, or the like.

Figure 3:
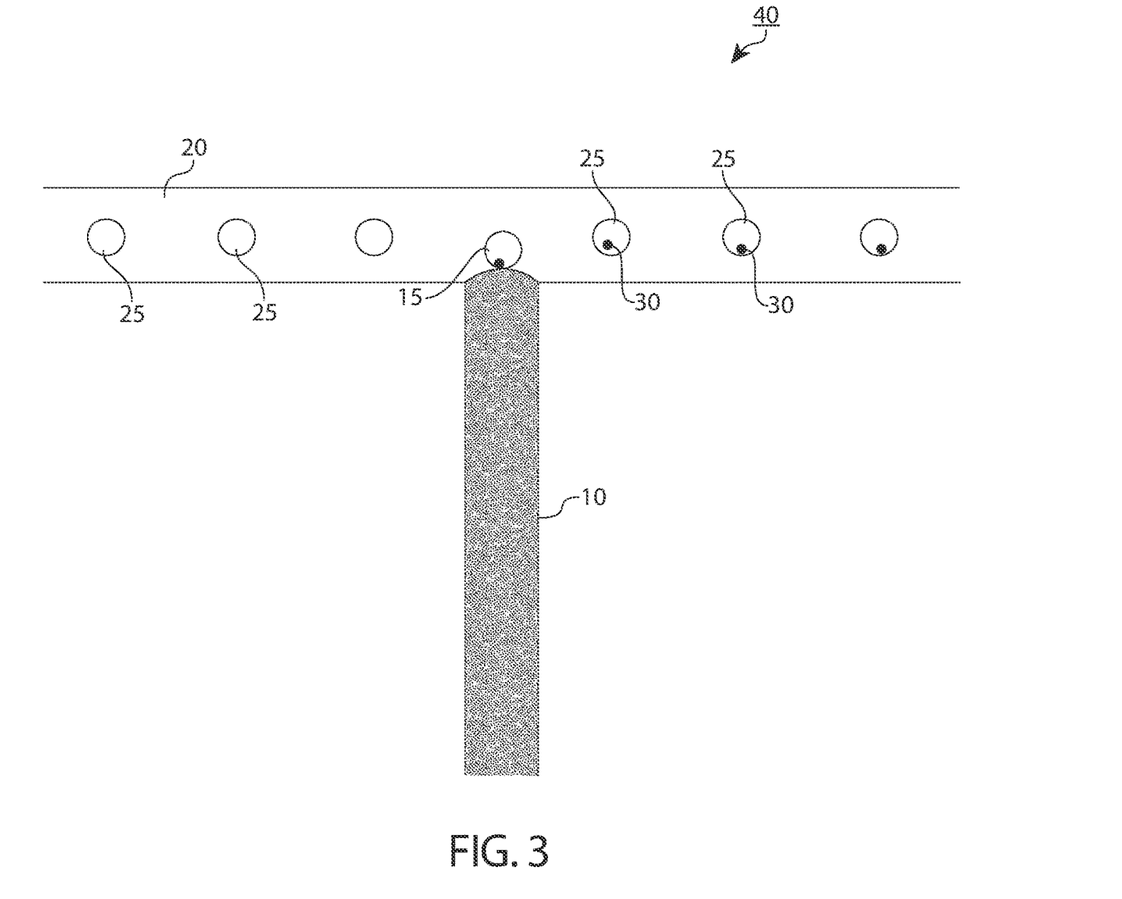
FIG. 3 illustrates a device in accordance with another embodiment of the invention.

One example of an aspect of the invention is now described with respect to FIG. 3. As will be discussed in more detail below, in other embodiments, other configurations may be used as well. In this figure, in microfluidic system 40, a first channel 10 containing a first fluid intersects a second channel 20 at an intersection 15. The channels may be of the same, or different, cross-sectional diameters or areas. Flowing through channel 20 are a plurality of microfluidic droplets 25 of a second fluid, which may be of the same or different diameters or volumes, e.g., contained within a suitable carrying fluid. In some cases, the droplets may substantially monodisperse, and may partially or completely fill the channel 20. Upon reaching intersection 15 (e.g., a T-intersection), the first fluid from first channel 10 may be transported into the droplets. The fluid may be transported into the channel, for example, using electric fields such as those discussed in Int. Pat. Apl. Pub. No. WO 2010/151776, acoustic waves such as those discussed in Int. Pat. Apl. Pub. No. WO 2015/200616, via diffusion, or other suitable techniques. (Each of these is incorporated herein by reference in its entirety.)

In some cases, the first fluid in first channel 10 contains a gel precursor. The gel precursor can be caused to form a gel 30, e.g., within microfluidic droplets 25. Typically, the fluid in first channel 10 will mix with the second fluid contained within microfluidic droplets 25, e.g., if the fluids are the same or at least substantially miscible. Thus, causing the first fluid to form a gel will cause the entire droplet to form a gel. However, surprisingly, in some aspects of the invention as discussed herein, a gel particle can be formed inside of the microfluidic droplet, i.e., the microfluidic droplet remains a liquid except for where the gel particle has formed within the droplet due to the first fluid. This can occur in some cases even if the fluids are substantially miscible with each other. Without wishing to be bound by any theory, it is believed that if the concentration of gel precursor within the fluid is sufficiently high, the fluids are not able to mix, e.g., due to increases in viscosity and/or surface tension associated with the fluids; accordingly, the gel precursor may be caused to solidify before it has sufficient time to mix or diffuse within the microfluidic droplet, thereby forming a gel particle within the microfluidic droplet.

Thus, in some cases, the gel may be present in the first fluid at a sufficiently high concentration as to prevent substantial mixing upon insertion into a second fluid, e.g., contained within a microfluidic droplet. For instance, the gel precursor may be present within the first fluid, prior to insertion within the microfluidic droplets, at a concentration of at least about 0.3 vol %, at least about 0.5 vol %, at least about 0.7 vol %, at least about 1 vol %, at least about 2 vol %, at least about 3 vol %, at least about 4 vol %, at least about 5 vol %, at least about 7 vol %, at least about 10 vol %, at least about 15 vol %, at least about 20 vol %, or at least about 25 vol %. In some cases, the concentration may also be no more than about 75 vol % or no more than about 50 vol %.

In one set of embodiments, the gel precursor comprises agarose. The agarose may be solidified, for example, by cooling the droplet to below the gelling temperature of the agarose, e.g., a temperature of less than about 45° C. Other gelling temperatures are also possible for different types of agarose, e.g., low melt agarose gels. For instance, the gelling temperature may be less than about 40° C., less than about 35° C., less than about 30° C., less than about 25° C., or less than about 20° C. Many types of agarose gel are readily available commercially. Thus, for example, the droplets may be exposed to a temperature of less than about 45° C., or other temperatures as discussed herein, e.g., to cause the agarose to solidify. Any suitable technique may be used to cool the droplets, e.g., exposure to a refrigerated section, an ice bath, introduction of a cooler fluid into the carrying fluid containing the droplets, or the like.

In other embodiments, other gels may be used instead of and/or in addition to agarose. Examples of the production of droplets of fluid surrounded by a liquid or carrying fluid are described in International Patent Application Serial No. PCT/US2004/010903, filed Apr. 9, 2004 by Link, et al. and International Patent Application Serial No. PCT/US03/20542, filed Jun. 30, 2003 by Stone, et al., published as WO 2004/002627 on Jan. 8, 2004, each incorporated herein by reference. Those of ordinary skill in the art will be aware of suitable fluids for use with the first fluid, the second fluid, and/or the carrying fluid, for example, as discussed in these references. In some cases, the first fluid, the second fluid, and the carrying fluid are all substantially immiscible. However, in other cases, the first fluid and the second fluid may be substantially miscible, e.g., as discussed herein. In some embodiments, the first fluid and the second fluid may even be the same or substantially the same, e.g., except for the presence of a gel precursor in the first fluid.

Certain aspects of the present invention relate to the injection of fluids into droplets, for example, in microfluidic systems. In some cases, relatively small amounts of fluid may be injected or transported into a droplet. For instance, the volume injected or transported may be less than about 10 microliters, less than about 1 microliter, less than about 100 nanoliters, less than about 10 nanoliters, less than about 1 nanoliter, less than about 100 picoliters, less than about 10 picoliters, less than about 1 picoliter, etc. In some cases, fluid may be injected while the fluid in the second channel is in motion (i.e., flowing through a channel). In other cases, fluid may be injected while the fluid in the channel is held stationary. For example, pressure in a channel may be controlled such that a droplet is urged to an intersection between the first channel and a second channel. The pressure and/or fluid flow within the second channel may then be decreased such that the droplet is then held stationary at the intersection, thereby allowing a desired amount of fluid to be injected or transported into the droplet. The pressure may then be increased and/or fluid flow may be controlled to urge the droplet away from the intersection once a desired amount of fluid has been injected or transported into the droplet. In some instances, the second channel may be configured, e.g., with a pump or other pressure control device such that fluid can be forcibly injected from the first channel, e.g., to a fluidic droplet, for example, without reliance on a difference in radii of curvature of the interface, or the like.

The flow velocity of droplets within a channel may be determined in some embodiments by factors such as the pressure or the pressure difference between the fluidic droplet in the first channel and the fluid in the second channel, the fluid pressure in one or both channels, the size of the orifice between the first channel and the second channel, the angle of intersection between the first and second channels, etc., e.g., as discussed above. The fluid pressure may be controlled using any suitable technique, for example, using a pump, siphon pressure, acoustic waves, or the like.

The first channel may intersect the second channel at an intersection at any point along the second channel. At the point of intersection between the first channel and the second channel, the first channel may meet the second channel via an orifice in some embodiments, i.e., a portion of the first channel at the intersection with the second channel may have a cross-sectional area that is smaller than the cross-sectional area of the first channel leading up to the intersection. In other embodiments, however, no orifice may be present, or the cross-sectional area of the first channel may even be relatively larger in some cases. The orifice, if present, may be of any shape, for example circular, elliptical, triangular, rectangular, etc., and may be positioned in any suitable position in the first channel, e.g., at an end or on a side of the first channel.

The orifice, if present, may have a cross-sectional area that is the same, greater than, or less than the cross-sectional area of the second channel at the intersection. In some cases, the cross-sectional area of the orifice is less than about 90%, less than about 80%, less than about 70%, less than about 60%, less than about 50%, less than about 40%, less than about 30%, less than about 20%, or less than about 10% of the cross-sectional area of the second channel at the intersection. The orifice may also have an average cross-sectional dimension less than about 100 microns, less than about 30 microns, less than about 10 microns, less than about 3 microns, less than about 1 micron, less than about 300 nm, less than about 100 nm, less than about 30 nm, less than about 10 nm, etc. The orifice may be flush with an intersecting wall of the first channel (i.e., the orifice may be defined by a lack of a portion of a wall of the first channel). In some cases, the orifice may be in a position that protrudes into the first channel.

In some cases, the first or main channel may have a cross-sectional area (i.e., defined perpendicular to fluid flow within the channel) that does not change substantially as the channel approaches the intersection. In other instances, however, the cross-sectional area may increase or decrease (i.e., constrict) as the first channel approaches the intersection. For example, the cross-sectional area of the first channel may decrease approaching the intersection.

As mentioned, the volume of fluid injected or transported may be controlled using any suitable technique, for example, by controlling the frequency, duration, intensity, timing, angle, etc. of acoustic waves, electric fields, etc. applied to the interface. For instance, in some embodiments, the flow rate of fluid in the first channel can be used to control the volume of fluid injected or transported into the droplet. In some cases, this can be controlled since the flow rate of fluid in the first channel controls the flow rate of fluidic droplets in the first channel, which thereby controls the amount of time that the fluidic droplets are present at the intersection and/or exposed to fluid in the second channel.

In some embodiments, the volume of fluid may be controlled by controlling the residence time of a first fluid in proximity to a second fluid, e.g., by controlling the residence time of a fluid in the second channel and positioned in front of the first channel. As a non-limiting example, the residence time of a fluidic in a droplet in the second channel positioned in front of the first channel may be controlled by varying the flow rate of fluid in the second channel. That is, a longer residence time may be achieved by slowing the flow rate or even stopping the flow of the fluid in the second channel. Likewise, a shorter residence time may be achieved by increasing the flow rate of the fluid in the second channel.

In another set of embodiments, the duration of the electric field and/or acoustic waves, e.g., while a droplet is positioned in an intersection of first and second channels may by varied. For example, to allow more fluid to be transported, the interface may be disrupted for a longer period of time. To allow a smaller amount of fluid transport, the interface may be disrupted for a shorter period of time.

Thus, in some embodiments, fluid may be injected or transported into a fluidic channel, e.g., in a fluidic droplet contained within the channel. In addition, as discussed, other configurations of two or more channels may be used in addition to, or instead of, the T-junction shown in FIG. 1.

For example, in one set of embodiments, the fluid may be injected or transported into the fluidic droplet using a needle such as a microneedle, a nozzle, an orifice, a tube, or other such devices. In another set of embodiments, the fluid may be injected directly into a fluidic droplet using a fluidic channel as the fluidic droplet comes into contact with the fluidic channel. For instance, in certain embodiments, a second channel containing a fluid may be intersected by a first channel at an intersection, or vice versa. The intersection may be, for example, a T-junction, a Y-junction, or the like. Fluid from the first channel may be injected or transported into the second channel, for example, using acoustic waves, electric fields, etc. For example, when a droplet contained within the second channel passes through the intersection, fluid from the first channel may be urged into the intersection, thereby entering the droplet and causing injection or transport of fluid into the droplet to occur.

It should be noted that, since this process may be controlled electronically in some cases, rapid droplet injection may be achieved in some cases, e.g., using suitable acoustic waves or electric fields. For instance, at least about 10 droplets per second may be injected in some cases, and in other cases, at least about 20 droplets per second, at least about 30 droplets per second, at least about 100 droplets per second, at least about 200 droplets per second, at least about 300 droplets per second, at least about 500 droplets per second, at least about 750 droplets per second, at least about 1000 droplets per second, at least about 1500 droplets per second, at least about 2000 droplets per second, at least about 3000 droplets per second, at least about 5000 droplets per second, at least about 7500 droplets per second, at least about 10,000 droplets per second or more droplets per second may be created in such a fashion.

In some embodiments, the droplets and/or the injected fluids may contain cells or other species. In some cases, a fluid to be injected into a droplet may contain a species that is desired to be injected into the droplet, e.g., an injected fluid may be used to add a species to a droplet. Examples of species include, but are not limited to, a chemical, biochemical, or biological entity, a cell, a particle, a bead, gases, molecules, a pharmaceutical agent, a drug, DNA, RNA, proteins, a fragrance, a reactive agent, a biocide, a fungicide, a pesticide, a preservative, or the like. Thus, the species can be any substance that can be contained in a fluid and can be differentiated from the fluid containing the species. For example, the species may be dissolved or suspended in the fluid. The species may be present in one or more of the fluids. If the fluids contain droplets, the species can be present in some or all of the droplets. Additional non-limiting examples of species that may be present include, for example, biochemical species such as nucleic acids such as siRNA, RNAi and DNA, proteins, peptides, or enzymes. Still other examples of species include, but are not limited to, nanoparticles, quantum dots, fragrances, proteins, indicators, dyes, fluorescent species, chemicals, or the like. As yet another example, the species may be a drug, pharmaceutical agent, or other species that has a physiological effect when ingested or otherwise introduced into the body, e.g., to treat a disease, relieve a symptom, or the like. In some embodiments, the drug may be a small-molecule drug, e.g., having a molecular weight of less than about 1000 Da or less than about 2000 Da.

In some embodiments, the droplets are relatively monodisperse, or the droplets may have relatively uniform cross-sectional diameters in certain embodiments. In some embodiments, the droplets may have an overall average diameter and a distribution of diameters such that no more than about 5%, no more than about 2%, or no more than about 1% of the particles or droplets have a diameter less than about 90% (or less than about 95%, or less than about 99%) and/or greater than about 110% (or greater than about 105%, or greater than about 101%) of the overall average diameter of the plurality of droplets.

In some embodiments, the droplets may have an average diameter of, for example, less than about 1 mm, less than about 500 micrometers, less than about 200 micrometers, less than about 100 micrometers, less than about 75 micrometers, less than about 50 micrometers, less than about 25 micrometers, less than about 10 micrometers, or less than about 5 micrometers in some cases. The average diameter may also be at least about 1 micrometer, at least about 2 micrometers, at least about 3 micrometers, at least about 5 micrometers, at least about 10 micrometers, at least about 15 micrometers, or at least about 20 micrometers in certain cases. In some cases combinations of these are also possible, e.g., the droplets may have an average diameter of between about 1 micrometer and about 1 mm. The "average diameter" of a plurality or series of droplets is the arithmetic average of the average diameters of each of the droplets. Those of ordinary skill in the art will be able to determine the average diameter (or other characteristic dimension) of a plurality or series of droplets, for example, using laser light scattering, microscopic examination, or other known techniques. The diameter of a droplet, in a non-spherical droplet, may be taken as the diameter of a perfect sphere having the same volume as the droplet.

In some embodiments, a first fluid may be more hydrophilic (or more hydrophobic) relative to a second fluid, and the first and the second fluids may be substantially immiscible. Thus, the first fluid can from a discrete droplet within the second fluid (or vice versa), e.g., without substantial mixing of the first fluid and the second fluid (although some degree of mixing may nevertheless occur under some conditions). In some embodiments, two fluids are immiscible, or not miscible, with each other when one is not soluble in the other to a level of at least 10% by weight at the temperature and under the conditions at which the droplets are produced. For instance, two fluids may be selected to be immiscible within the time frame of the formation of the fluidic droplets within the other fluid. In some cases, a first fluid is hydrophilic while another fluid (e.g., carrying the first fluid) is hydrophobic or immiscible with the first fluid. Examples of hydrophilic liquids include, but are not limited to, water and other aqueous solutions comprising water, such as cell or biological media, ethanol, salt solutions, etc. Examples of hydrophobic liquids include, but are not limited to, oils such as hydrocarbons, silicon oils, fluorocarbon oils, organic solvents etc. However, in other embodiments, the fluids may be substantially miscible. For instance, two or more fluids may be hydrophilic or both hydrophobic. In some embodiments, for instance, a first fluid to be injected into a second fluid, and the second fluid, may both be hydrophilic while a carrying fluid containing droplets of the second fluid is hydrophobic, or vice versa.

In some aspects, one or more electrodes are provided that can apply an electric field to an intersection of a first channel and a second channel. In some cases, the electrodes may be positioned such that the electrodes create an electric field maximum that contains the intersection, or at least is proximate the intersection. For instance, the electrodes may be positioned to create an electric field or an electric field maximum located where the second channel intersects with the first channel, or such that the interface between two fluids in the channels experiences a suitable electric field. The electrodes may be positioned relative to the channels in a variety of configurations. In some examples, an electrode may be positioned essentially opposite the first channel or the second channel. Alternatively, an electrode may be positioned substantially to one side of the first channel or the second channel. In some embodiments, an electrode may be positioned above or below the first channel or the second channel (e.g., in another layer of the device).

An electrode as discussed herein may be fabricated from any suitable material, and if two or more electrodes are present, the electrodes may be formed from the same or different materials. Non-limiting examples of electrode materials include metals, metalloids, semiconductors, graphite, conducting polymers, and the like. The electrode may have any shape suitable for applying an electric field.

In some cases, an electrode may have an essentially rectangular shape. As another example, an electrode may be elongated and have a tip defined as a region of the electrode closest to an intersection between a first channel and a second channel. In some embodiments, the tip of an electrode may have a width that is similar to a width of the second channel. In other embodiments, the tip of an electrode may have a width substantially larger than a width of the second channel. The electrode shape can be flat, V-shaped, or any other suitable shape, such as the shapes discussed herein. In some cases, the electrode is constructed such that an electric field maximum is created, e.g., in the intersection or proximate the intersection.

The electric field produced by the electrodes, in some embodiments, is generated using an electric field generator, i.e., a device or system able to create an electric field that can be applied to the fluid, e.g., via one or more electrodes. For example, the electric field generator may include a voltage source and one or more electrodes. Voltage sources include batteries, wall current, fuel cells, or the like, and a wide variety of voltage sources are commercially available. The electric field generator may produce an AC field (i.e., one that varies periodically with respect to time, for example, sinusoidally, sawtooth, square, etc.), a DC field (i.e., one that is constant with respect to time), a pulsed field, etc. The electric field generator may be constructed and arranged to create an electric field within a fluid contained within a channel or a microfluidic channel The electric field generator may be integral to or separate from the fluidic system containing the channel, according to some embodiments. As used herein, "integral" means that portions of the components integral to each other are joined in such a way that the components cannot be manually separated from each other without cutting or breaking at least one of the components. In addition, in some cases, the electric field may be automatically controlled, e.g., by aid of a computer or an automatic device.

As mentioned, in some instances, the electric field is applied to an intersection between a first channel and a second channel; for example, the electric field may be applied to an intersection between a first channel and a second channel. The electric field may be applied continuously, periodically, or intermittently, depending on the embodiment, and may be AC, DC, etc. For example, while an intersection is exposed to an electric field, a fluidic droplet may be urged into or through the intersection. The electric field may be applied to disrupt the interface formed between the fluidic droplet and, for example, a fluid in the second channel, e.g., as discussed above, thereby allowing fluid exchange from the second channel into the first channel to occur. As another example, by controlling the electric field, fluid from the second channel may be urged into the first channel to create one or more new droplets contained within the first channel.

The voltage applied to the electrodes may be any suitable voltage for disrupting a fluidic interface. For example, the voltage may be between 0.1 V and 10,000 V, between 0.1 V and 1,000 V, between 0.1 V and 300 V, between 0.1 V and 100 V, between 0.1 V and 50 V, between 0.1 V and 30 V, between 0.1 V and 10 V, or the like. An applied voltage may be applied continuously, pulsatile, intermittently, randomly, etc. The pulses may be DC, or AC, with any suitable frequency, for example, frequencies in the hertz, kilohertz, or megahertz ranges, etc.

For example, in one embodiment, the electric field that is applied may be pulsed. For instance, the electric field may be applied when a fluidic droplet is present at an intersection, but not applied at other times. In another embodiment, the electric field is applied while a fluidic droplet is in front of the second channel. For example, the electric field may be applied for a period of time sufficient for injection and/or withdrawal of a specific volume of fluid, e.g., the electric field may on for a period of time and off for a period of time while the fluidic droplet is in front of the second channel.

By applying a voltage across the electrodes, e.g., via an electric field generator, an electric field may be created, which may be modeled as electric field lines passing from the positive electrode to the negative electrode. The electric field lines may pass through the interface between the fluids, for example, in the same direction as the flow during injection of a fluid from the second channel into the first channel. Other angles may be used in other embodiments. The electrodes may be positioned to center the electric field over the intersection, or offset from the center, for example, to generate a component of the electric field in a direction of a flow channel.

In some embodiments, a fluidic interface may be disrupted after a certain threshold electric field strength has been reached. The threshold electric field strength may be any minimum value able to disrupt the interface, and may vary by application. For example, factors such as the viscosity or density of the fluids contained within the channel, the flow rate of fluids within the channels, the geometry (e.g., sizes or dimensions) of the channels, the angle at which the channels meet at an intersection, the presence of other forces applied to the fluid, etc., may affect the threshold electric field strength for a particular application. Non-limiting examples of electric field strength for disrupting an interface include electric field strengths greater than about 0.01 V/micrometer, greater than about 0.03 V/micrometer, greater than about 0.1 V/micrometer, greater than about 0.3 V/micrometer, greater than about 1 V/micrometer, greater than about 3 V/micrometer, greater than about 10 V/micrometer, etc. It should be understood that values outside these ranges may also be used in some instances. In some cases, the amount of fluid transfer may be essentially constant as a function of voltage above the threshold voltage. In other embodiments, the amount of interface disruption generally increases as electric field strength increases.

In certain aspects, acoustic waves, such as surface acoustic waves, are applied, e.g., to an intersection to cause fluid transport into a droplet. A surface acoustic wave ("SAW") is, generally speaking, an acoustic wave able to travel along the surface of a material exhibiting elasticity, with an amplitude that typically decays exponentially with depth into the material. By selecting suitable acoustic waves, pressure changes may be induced in the fluid, which can be used to manipulate the fluid in some cases. For example, acoustic waves applied to a fluid may increase or decrease the pressure on the fluid, which may affect the position of a fluidic interface between the fluid and another fluid. In some cases, the interface may be disrupted upon application of the acoustic waves, which may cause the interface to break or allow fluid mixing to occur.

The acoustic waves may be applied at varying amplitudes or powers in some cases. In some cases, the pressure changes created in the fluid may be a function of the power of the acoustic wave. For example, the acoustic wave may have a power of at least about 0 dBm, at least about 3 dBm, at least about 6 dBm, at least about 9 dBm, at least about 12 dBm, at least about 15 dBm, at least about 20 dBM, etc. The surface acoustic wave may also have any suitable average frequency, in various embodiments. For example, the average frequency of the surface acoustic wave may be between about 100 MHz and about 200 MHz, between about 130 MHz and about 160 MHz, between about 140 MHz and about 150 MHz, between about 100 MHz and about 120 MHz, between about 120 MHz and about 140 MHz, between about 140 MHz and about 160 MHz, between about 160 MHz and about 180 MHz, or between about 180 MHz and about 200 MHz or the like, and/or combinations thereof. In other embodiments, the frequency may be between about 50 Hz and about 100 KHz, between about 100 Hz and about 2 kHz, between about 100 Hz and about 1,000 Hz, between about 1,000 Hz and about 10,000 Hz, between about 10,000 Hz and about 100,000 Hz, or the like, and/or combinations thereof. In some cases, the frequency may be at least about 10 Hz, at least about 30 Hz, at least about 50 Hz, at least about 100 Hz, at least about 300 Hz, at least about 1,000 Hz, at least about 3,000 Hz, at least about 10,000 Hz, at least about 30,000 Hz, at least about 100,000 Hz, at least about 300,000 Hz, at least about 1 MHz, at least about 3 MHz, at least about 10 MHz, at least about 30 MHz, at least about 100 MHz, at least about 300 MHz, or at least about 1 GHz or more in some embodiments. In certain instances, the frequency may be no more than about 1 GHz, no more than about 300 MHz, no more than about 100 MHz, no more than about 30 MHz, no more than about 10 MHz, no more than about 3 MHz, no more than about 1 MHz, no more than about 300,000 Hz, no more than about 100,000 Hz, no more than about 30,000 Hz, no more than about 10,000 Hz, no more than about 3,000 Hz, no more than about 1,000 Hz, no more than about 300 Hz, no more than about 100 Hz, or the like. Combinations of any of the above frequencies and/or other frequencies are also possible in some cases.

The acoustic waves may be applied at any suitable direction to the fluid, e.g., at an interface or an intersection. In some embodiments, acoustic waves may be applied orthogonally, or in a downstream direction or an upstream direction, relative to the flow of fluid in a channel. For example, acoustic waves may be applied to a channel, such as a microfluidic channel, in a direction of fluid flow within the channel, in a direction opposite of fluid flow within the channel, or in another direction (e.g., perpendicular to fluid flow within the channel). In other embodiments, the acoustic waves may be applied at any suitable angle relative to the microfluidic channel, for example, about 0°, about 5°, about 10°, about 20°, about 30°, about 40°, about 50°, about 60°, about 70°, about 80°, about 90°, about 100°, about 110°, about 120°, about 130°, about 140°, about 150°, about 160°, about 170°, about 175°, about 180° etc. In some cases, more than one acoustic wave may be applied to control fluid flow within the channel. The acoustic waves may be applied at the same, or different regions of a channel, depending on the application. For instance, in some cases, a first acoustic wave and a second acoustic wave may be applied to overlapping portions of a fluid, e.g., at an interface or a junction, or a first acoustic wave may be applied to a first portion of a fluid within a channel, and the second acoustic wave may be applied to a second portion of the fluid within the channel. If more than one acoustic wave is applied to a fluid, the acoustic waves may be applied in any suitable order, e.g., simultaneously, sequentially, periodically, etc.

Without wishing to be bound by any theory, it should be noted that acoustic waves may be very rapidly controlled, e.g., electrically, and typically can be applied to fluids at very small time scales. Thus, individual regions of fluids, e.g., droplets of fluid as is discussed herein, may be controlled to an arbitrary degree, e.g., without affecting other regions or droplets of fluids, even nearby or adjacent ones. For example, an acoustic wave may be applied to a first region or droplet, then no acoustic wave may be applied, or an acoustic wave of a different magnitude and/or frequency, applied to an adjacent or nearby second region or droplet. Thus, each region or droplet can be independently controlled, without affecting adjacent or nearby regions or droplets. In contrast, in other microfluidic systems, such a high per-region or per-droplet basis for control of fluid or droplet characteristics cannot typically be achieved.

In addition, in some cases, the acoustic waves may be applied continuously, or intermittently or "pulsed." In some cases, the acoustic waves may be intermittently applied at a frequency, or in a way, such that individual droplets or regions are affected by the acoustic waves, but other droplets or regions are not. In addition, in some cases, the acoustic waves may be constant (i.e., having a fixed magnitude), or the acoustic wave may have an amplitude whose magnitude varies in time, e.g., the acoustic wave may have an amplitude that varies independently of the frequency of the acoustic wave.

As discussed, the acoustic waves may be applied to any suitable channel. In one set of embodiments, the acoustic waves are applied to a fluid contained within a channel, such as a microfluidic channel, to control the fluid. Various examples of microfluidic channels are discussed herein. More than one fluid may be present within the channel, in some instances, e.g., flowing as separate phases (for example, side-by-side, as droplets of a first fluid contained within a second fluid, etc.). As discussed herein, non-limiting examples of such channels include straight channels, bent channels, droplet-making channel configurations, and the like.

In some embodiments, the width of the channel may be chosen such that it is no more than about the full width at half maximum (FWHM) or 90% of the maximum of the acoustic wave or acoustic wave front. Without wishing to be bound by any theory, it is believed that such dimensions of the channel, relative to the acoustic wave or acoustic wave front, may decrease flow vortices that may be formed, which may decrease efficiency.

In some cases, the surface acoustic waves may be created using a surface acoustic wave generator such as an interdigitated transducer, and/or a material such as a piezoelectric substrate. The piezoelectric substrate may be isolated from the substrate except at or proximate the location where the acoustic waves are to be applied, e.g., proximate a first or second channel, proximate a junction of two or more channels, etc. At such locations, the substrate may be coupled to the piezoelectric substrate (or other material) by one or more coupling regions.

Any suitable technique may be used to create a surface acoustic wave, in various aspects of the invention. In some cases, the surface acoustic waves may be created using a surface acoustic wave generator such as an interdigitated transducer, and/or a material such as a piezoelectric substrate. The piezoelectric substrate may be isolated from the substrate except at or proximate the location where the acoustic waves are to be applied, e.g., proximate a first or second channel, proximate a junction of two or more channels, etc. At such locations, the substrate may be coupled to the piezoelectric substrate (or other material) by one or more coupling regions.

In some embodiments, the surface acoustic wave may be created by a generator attached to the surface of a material. In certain embodiments, the surface acoustic wave is created by using an interdigitated electrode or transducer able to convert electrical signals into acoustic waves able to travel along the surface of a material, and in some cases, the frequency of the surface acoustic waves may be controlled by controlling the spacing of the finger repeat distance of the interdigitated electrode or transducer. The surface acoustic waves can be formed on a piezoelectric substrate or other material that may be coupled to a microfluidic substrate at specific locations, e.g., at locations within the microfluidic substrate where injection or mixing is to take place. Suitable voltages (e.g., sinusoidal or other periodically varying voltages) are applied to the piezoelectric substrate, which converts the electrical signals into mechanical vibrations, i.e., surface acoustic waves or sound. The sound is then coupled to the microfluidic substrate, e.g., from the surface of the material. In the microfluidic substrate, the vibrations pass into liquid within microfluidic channels in the microfluidic substrate (e.g., to a liquid containing droplets), which give rise to internal streaming within the fluid. Thus, by controlling the applied voltage, streaming within the microfluidic channel may be controlled, which may be used to control droplets within the microfluidic channel, e.g., to cause fluid injection or mixing to occur.

An interdigitated transducer typically comprises one, two, or more electrodes containing a plurality of "fingers" extending away from the electrode, wherein at least some of the fingers are interdigitated. The fingers may be of any length, and may independently have the same or different lengths. The fingers may be spaced on the transducer regularly or irregularly. In some cases, the fingers may be substantially parallel, although in other embodiments they need not be substantially parallel. For example, in one set of embodiments, the interdigitated transducer is a tapered interdigitated transducer. In some cases, the fingers in a tapered interdigitated transducer may be arranged such that the fingers are angled inwardly. Examples of such transducers may be found, e.g., in International Patent Application No. PCT/US2011/048804, filed Aug. 23, 2011, entitled "Acoustic Waves in Microfluidics," by Weitz, et al., published as WO 2012/027366 on Mar. 1, 2012; and International Patent Application No. PCT/US2013/047829, filed Jun. 26, 2013, entitled "Control of Entities Such as Droplets and Cells Using Acoustic Waves," by Weitz, et al., published as WO 2014/004630 on Jan. 3, 2014, each incorporated herein by reference in their entireties.

The interdigitated electrode typically includes of two interlocking comb-shaped metallic electrodes that do not touch, but are interdigitated. The electrodes may be formed from any suitable electrode material, for example, metals such as gold, silver, copper, nickel, or the like. The operating frequency of the interdigitated electrode may be determined, in some embodiments, by the ratio of the sound velocity in the substrate to twice the finger spacing. For instance, in one set of embodiments, the finger repeat distance may be between about 10 micrometers and about 40 micrometers, between about 10 micrometers and about 30 micrometers, between about 20 micrometers and about 40 micrometers, between about 20 micrometers and about 30 micrometers, or between about 23 micrometers and about 28 micrometers.

The interdigitated electrode may be positioned on a piezoelectric substrate, or other material able to transmit surface acoustic waves, e.g., to a coupling region. The piezoelectric substrate may be formed out of any suitable piezoelectric material, for example, quartz, lithium niobate, lithium tantalate, lanthanum gallium silicate, etc. In one set of embodiments, the piezoelectric substrate is anisotropic, and in some embodiments, the piezoelectric substrate is a Y-cut $LiNbO_3$ material.

The piezoelectric substrate may be activated by any suitable electronic input signal or voltage to the piezoelectric substrate (or portion thereof). For example, the input signal may be one in which a periodically varying signal is used, e.g., to create corresponding acoustic waves. For instance, the signals may be sine waves, square waves, sawtooth waves, triangular waves, or the like. The frequency may be for example, between about 50 Hz and about 100 KHz, between about 100 Hz and about 2 kHz, between about 100 Hz and about 1,000 Hz, between about 1,000 Hz and about 10,000 Hz, between about 10,000 Hz and about 100,000 Hz, or the like, and/or combinations thereof. In some cases, the frequency may be at least about 50 Hz, at least about 100 Hz, at least about 300 Hz, at least about 1,000 Hz, at least about 3,000 Hz, at least about 10,000 Hz, at least about 30,000 Hz, at least about 100,000 Hz, at least about 300,000 Hz, at least about 1 MHz, at least about 3 MHz, at least about 10 MHz, at least about 30 MHz, at least about 100 MHz, at least about 300 MHz, or at least about 1 GHz or more in some embodiments. In certain instances, the frequency may be no more than about 1 GHz, no more than about 300 MHz, no more than about 100 MHz, no more than about 30 MHz, no more than about 10 MHz, no more than about 3 MHz, no more than about 1 MHz, no more than about 300,000 Hz, no more than about 100,000 Hz, no more than about 30,000 Hz, no more than about 10,000 Hz, no more than about 3,000 Hz, no more than about 1,000 Hz, no more than about 300 Hz, no more than about 100 Hz, or the like.

The interdigitated electrode may be positioned on the piezoelectric substrate (or other suitable material) such that acoustic waves produced by the interdigitated electrodes are directed at a region of acoustic coupling between the piezoelectric substrate and the microfluidic substrate. For example, the piezoelectric substrate and the microfluidic substrate may be coupled or physically bonded to each other, for example, using ozone plasma treatment, or other suitable techniques. In some cases, the rest of the piezoelectric substrate and the microfluidic substrate are at least acoustically isolated from each other, and in certain embodiments, the piezoelectric substrate and the microfluidic substrate are physically isolated from each other. Without wishing to be bound by any theory, it is believed that due to the isolation, acoustic waves created by the interdigitated electrode and the piezoelectric substrate do not affect the microfluidic substrate except at regions where it is desired that the acoustic waves are applied, e.g., at a channel or a junction.

The coupling region may have any suitable shape and/or size. The coupling region may be round, oval, or have other shapes, depending on the embodiment. In some cases, two, three, or more coupling regions may be used. In one set of embodiments, the coupling region is sized to be contained within a microfluidic channel. In other embodiments, however, the coupling region may be larger. The coupling region may be positioned within a channel or proximate to the channel, in some embodiments.

In some cases, control of the droplets into one of the channels may be achieved by using a tapered interdigitated transducer. A tapered interdigitated transducer may allow relatively high control of the location at which a SAW is applied to a channel, in contrast to an interdigitated transducer where all of the fingers are parallel to each other and the spacing between electrodes is constant. Without wishing to be bound by any theory, it is believed that the location which a SAW can be applied by an interdigitated transducer is controlled, at least in part, by the spacing between the electrodes. By controlling the potential applied to the interdigitated transducer, and thereby controlling the resonance frequency of the applied SAW, the position and/or the strength of the SAW as applied by the interdigitated transducer may be correspondingly controlled. Thus, for example, applying a first voltage to an interdigitated transducer may cause a first resonance frequency of the resulting SAW to be applied (e.g., within a channel), while applying a second voltage may cause a second resonance frequency of the resulting SAW to be applied to a different location (e.g., within the channel). As another example, a plurality of coupling regions may be used, e.g., in combination with one or more tapered interdigitated transducers.

A variety of definitions are now provided which will aid in understanding various aspects of the invention. Following, and interspersed with these definitions, is further disclosure that will more fully describe the invention.

As noted, various embodiments of the present invention relate to droplets of fluid. The droplets may be of substantially the same shape and/or size, or of different shapes and/or sizes, depending on the particular application. It should be noted that a droplet is not necessarily spherical, but may assume other shapes as well, for example, depending on the external environment. A droplet, in some cases, may have a cross-sectional dimension that is smaller than the channel containing the droplet, although in other cases, the droplet may completely fill a cross-sectional portion of the channel.

As mentioned, in some, but not all embodiments, the systems and methods described herein may include one or more microfluidic components, for example, one or more microfluidic channels. "Microfluidic," as used herein, refers to a device, apparatus or system including at least one fluid channel having a cross-sectional dimension of less than 1 mm. In some cases, the channel may have a ratio of length to largest cross-sectional dimension of at least 3:1. A "microfluidic channel," as used herein, is a channel meeting these criteria. The "cross-sectional dimension" of the channel is measured perpendicular to the direction of fluid flow within the channel. Thus, some or all of the fluid channels in microfluidic embodiments of the invention may have maximum cross-sectional dimensions less than 2 mm, and in certain cases, less than 1 mm. In one set of embodiments, all fluid channels containing embodiments of the invention are microfluidic or have a largest cross sectional dimension of no more than 2 mm or 1 mm. In certain embodiments, the fluid channels may be formed in part by a single component (e.g. an etched substrate or molded unit). Of course, larger channels, tubes, chambers, reservoirs, etc. can be used to store fluids and/or deliver fluids. In one set of embodiments, the maximum cross-sectional dimension of the channel(s) containing embodiments of the invention is less than 500 microns, less than 200 microns, less than 100 microns, less than 50 microns, or less than 25 microns.

A channel can have any cross-sectional shape (circular, oval, triangular, irregular, square or rectangular, or the like) and can be covered or uncovered. In embodiments where it is completely covered, at least one portion of the channel can have a cross-section that is completely enclosed, or the entire channel may be completely enclosed along its entire length with the exception of its inlet(s) and/or outlet(s). A channel may also have an aspect ratio (length to average cross sectional dimension) of at least 2:1, more typically at least 3:1, 5:1, 10:1, 15:1, 20:1, or more. An open channel generally will include characteristics that facilitate control over fluid transport, e.g., structural characteristics (an elongated indentation) and/or physical or chemical characteristics (hydrophobicity vs. hydrophilicity) or other characteristics that can exert a force (e.g., a containing force) on a fluid. The fluid within the channel may partially or completely fill the channel. In some cases where an open channel is used, the fluid may be held within the channel, for example, using surface tension (i.e., a concave or convex meniscus).

The channel may be of any size, for example, having a largest dimension perpendicular to fluid flow of less than about 5 mm or 2 mm, or less than about 1 mm, or less than about 500 microns, less than about 200 microns, less than about 100 microns, less than about 60 microns, less than about 50 microns, less than about 40 microns, less than about 30 microns, less than about 25 microns, less than about 10 microns, less than about 3 microns, less than about 1 micron, less than about 300 nm, less than about 100 nm, less than about 30 nm, or less than about 10 nm. In some cases the dimensions of the channel may be chosen such that fluid is able to freely flow through the article or substrate. The dimensions of the channel may also be chosen, for example, to allow a certain volumetric or linear flowrate of fluid in the channel. Of course, the number of channels and the shape of the channels can be varied by any method known to those of ordinary skill in the art. In some cases, more than one channel or capillary may be used. For example, two or more channels may be used, where they are positioned inside each other, positioned adjacent to each other, positioned to intersect with each other, etc.

The following are incorporated herein by reference: Int. Pat. Apl. Pub. No. WO 2010/151776, filed Jun. 25, 2010, entitled "Fluid Injection," by Weitz, et al.; and Int. Pat. Apl. Pub. No. WO 2015/200616, filed Jun. 25, 2015, entitled "Fluid Injection Using Acoustic Waves," by Weitz, et al. In addition, the following documents are incorporated herein by reference: U.S. patent application Ser. No. 11/360,845, filed Feb. 23, 2006, entitled "Electronic Control of Fluidic Species," by Link, et al., published as U.S. Patent Application Publication No. 2007/0003442 on Jan. 4, 2007; U.S. patent application Ser. No. 08/131,841, filed Oct. 4, 1993, entitled "Formation of Microstamped Patterns on Surfaces and Derivative Articles," by Kumar, et al., now U.S. Pat. No. 5,512,131, issued Apr. 30, 1996; priority to International Patent Application No. PCT/US96/03073, filed Mar. 1, 1996, entitled "Microcontact Printing on Surfaces and Derivative Articles," by Whitesides, et al., published as WO 96/29629 on Jun. 26, 1996; U.S. patent application Ser. No. 09/004,583, filed Jan. 8, 1998, entitled "Method of Forming Articles Including Waveguides via Capillary Micromolding and Microtransfer Molding," by Kim, et al., now U.S. Pat. No. 6,355,198, issued Mar. 12, 2002; International Patent Application No. PCT/US01/16973, filed May 25, 2001, entitled "Microfluidic Systems including Three-Dimensionally Arrayed Channel Networks," by Anderson, et al., published as WO 01/89787 on Nov. 29, 2001; U.S. Provisional Patent Application Ser. No. 60/392,195, filed Jun. 28, 2002, entitled "Multiphase Microfluidic System and Method," by Stone, et al.; U.S. Provisional Patent Application Ser. No. 60/424,042, filed Nov. 5, 2002, entitled "Method and Apparatus for Fluid Dispersion," by Link, et al.; U.S. Provisional Patent Application Ser. No. 60/461,954, filed Apr. 10, 2003, entitled "Formation and Control of Fluidic Species," by Link, et al.; International Patent Application No. PCT/US03/20542, filed Jun. 30, 2003, entitled "Method and Apparatus for Fluid Dispersion," by Stone, et al., published as WO 2004/002627 on Jan. 8, 2004; U.S. Provisional Patent Application Ser. No. 60/498,091, filed Aug. 27, 2003, entitled "Electronic Control of Fluidic Species," by Link, et al.; International Patent Application No. PCT/US2004/010903, filed Apr. 9, 2004, entitled "Formation and Control of Fluidic Species," by Link, et al., published as WO 2004/091763 on Oct. 28, 2004; International Patent Application No. PCT/US2004/027912, filed Aug. 27, 2004, entitled "Electronic Control of Fluidic Species," by Link, et al., published as WO 2005/021151 on Mar. 10, 2005; U.S. patent application Ser. No. 11/024,228, filed Dec. 28, 2004, entitled "Method and Apparatus for Fluid Dispersion," by Stone, et al., published as U.S. Patent Application Publication No. 2005-0172476 on Aug. 11, 2005; U.S. Provisional Patent Application Ser. No. 60/659,045, filed Mar. 4, 2005, entitled "Method and Apparatus for Forming Multiple Emulsions," by Weitz, et al.; U.S. Provisional Patent Application Ser. No. 60/659,046, filed Mar. 4, 2005, entitled "Systems and Methods of Forming Particles," by Garstecki, et al.; and U.S. patent application Ser. No. 11/246,911, filed Oct. 7, 2005, entitled "Formation and Control of Fluidic Species," by Link, et al.

Also incorporated herein by reference is U.S. Provisional Patent Application Ser. No. 62/360,143, filed Jul. 8, 2017, entitled "Formation of Colloids Within Droplets," by Weitz, et al.

The following examples are intended to illustrate certain embodiments of the present invention, but do not exemplify the full scope of the invention.

Example 1

This example shows an efficient and simple method to form monodispersed sub-hydrocolloid gel particles in fluid drops. This is particularly useful, for example, for making a gel particle library by exposing gel particles to different incubation conditions while keeping the original gel particle size. Firstly, a library of fluid drops with different conditions, such as different chemicals, drugs or nucleic acids, is prepared. These fluid drops are loaded into a microfluidic pico-injector (see, e.g., U.S. Pat. Apl. Pub. No. 2012/0132288, incorporated herein by reference in its entirety), spaced with oil containing surfactant.

Figure 1:
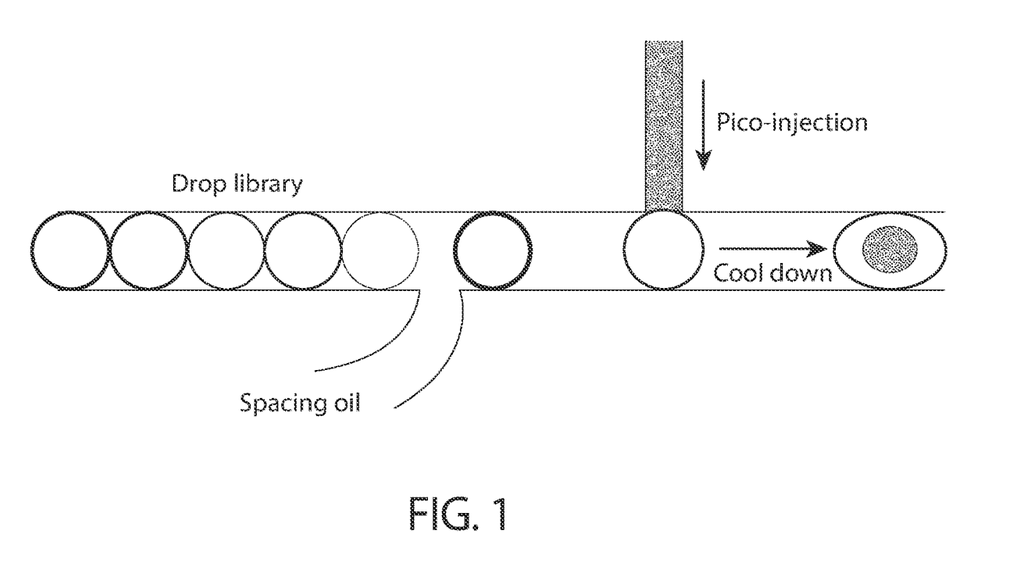
FIG. 1 illustrates a device in accordance with one embodiment of the invention.

Downstream, agarose gel solution containing species, such as cells, were electrically injected into fluid droplets. The droplets are collected into an Eppendorf tube placed in a 0° C. ice rack (FIG. 1). The drop size was found to be about 120 micrometers in diameter.

Figure 2A:
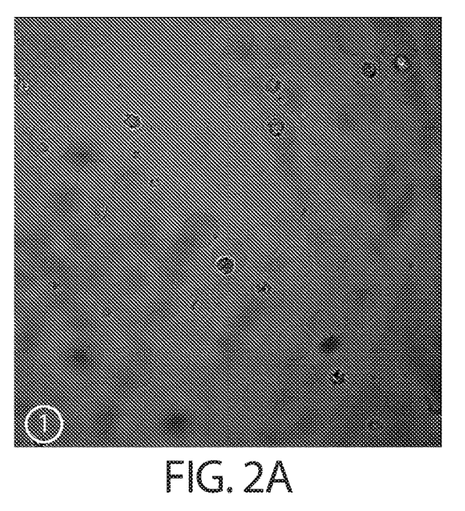
FIGS. 2A-2D illustrate gels produced in certain embodiments of the invention.
Figure 2B:
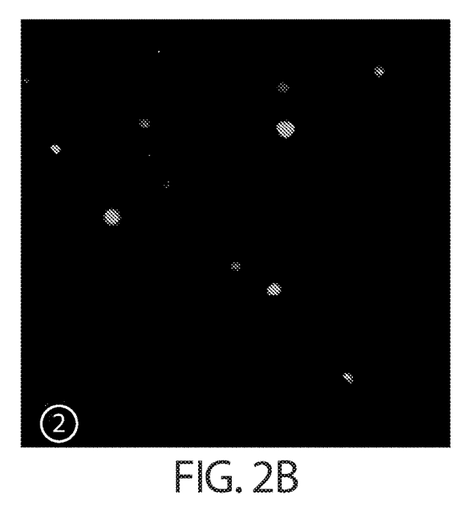
Figure 2C:
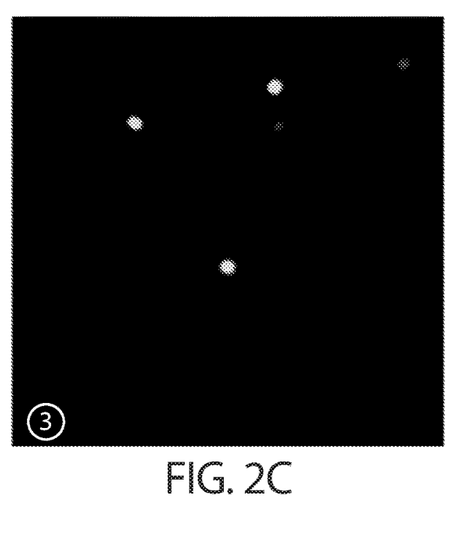
Figure 2D:
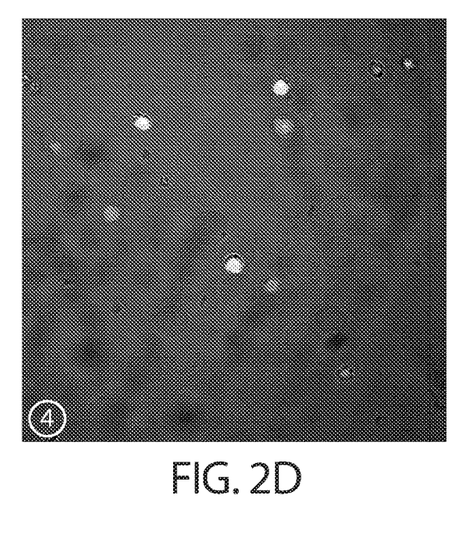

To observe the sub-hydrocolloid gel particles inside the drops, 1H, 1H, 2H, 2H-perfluoro-octanol (PFO) was added to the emulsion, followed by centrifugation at 1,500 rpm for 3 min. The resulting gel particles were in the upper layer while PFO and oil were found in the bottom due to their higher density. The sub-hydrocolloid gels and gels containing cells are about 50 micrometers, as shown in FIG. 2. In particular, FIG. 2A shows a bright field image of the gel particles; FIG. 2B shows dead cells (red channel) within the gel particles; FIG. 2C shows live cells (green channel) within the gel particles, and FIG. 2D shows a merged image of these.

In this work, it was unexpectedly shown that the agarose gel injected into a fluid drop was able to form into a separate gel particle, rather than dissolving or becoming dispersed within the drop. Without wishing to be bound by any theory, it is hypothesized that this occurs because the high concentration of gel in the inserted fluid has a surface tension that is too high to prevent the liquid from coming into gel particles. It was also shown that at agarose concentrations lower than 0.7%, no gel particles could be formed.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

When the word "about" is used herein in reference to a number, it should be understood that still another embodiment of the invention includes that number not modified by the presence of the word "about."

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A method, comprising:
    transporting a first fluid containing a gel precursor at at least 0.5 vol % into a microfluidic droplet containing a second fluid, wherein transporting the first fluid into the microfluidic droplet comprises applying an acoustic wave to an interface between the first fluid and the microfluidic droplet; and
    causing the gel precursor to solidify to form a gel particle contained within the second fluid in the microfluidic droplet.

2. The method of claim 1, wherein the gel precursor comprises agarose.

3. The method of claim 1, wherein the first fluid and the second fluid are substantially miscible.

4. The method of claim 1, wherein the microfluidic droplet containing the second fluid is contained in a carrying fluid.

5. The method of claim 1, wherein transporting the first fluid into the microfluidic droplet comprises creating a pressure difference between the first fluid and the microfluidic droplet sufficient to cause at least a portion of the first fluid to enter the microfluidic droplet.

6. The method of claim 1, wherein the first fluid is contained within a first microfluidic channel, the microfluidic droplets are contained within a second microfluidic channel intersecting the first microfluidic channel, and transport of the first fluid into the microfluidic droplet occurs at an intersection between the first microfluidic channel and the second microfluidic channel.

7. The method of claim 6, wherein the intersection is a T intersection, the first microfluidic channel ending at the intersection and the second microfluidic channel passing through the intersection.

8. The method of claim 6, wherein the second microfluidic channel connects to the intersection via an orifice having an area of no more than 50% of the average cross-sectional dimension of the second microfluidic channel.

9. The method of claim 1, wherein the microfluidic droplet has an average diameter of less than 1 mm.

10. The method of claim 1, wherein the microfluidic droplet is one of a plurality of substantially monodisperse microfluidic droplets.

11. The method of claim 1, wherein the microfluidic droplet has an average diameter of less than 75 micrometers.

12. A method, comprising:
transporting a first fluid containing a gel precursor at at least 0.5 vol % into a microfluidic droplet containing a second fluid; and
causing the gel precursor to solidify to form a gel particle contained within the second fluid in the microfluidic droplet,
wherein the first fluid is contained within a first microfluidic channel, the microfluidic droplet is contained within a second microfluidic channel intersecting the first microfluidic channel, and transport of the first fluid into the microfluidic droplet occurs at an intersection between the first microfluidic channel and the second microfluidic channel, and
wherein the intersection is a T intersection, the first microfluidic channel ending at the intersection and the second microfluidic channel passing through the intersection.

13. The method of claim 12, wherein transporting the first fluid into the microfluidic droplet comprises applying an electric field to an interface between the first fluid and the microfluidic droplet.

14. The method of claim 13, wherein the electric field is applied using two electrodes positioned on the same side of the second microfluidic channel.

15. The method of claim 13, wherein the electric field is applied using two electrodes positioned on opposite sides of the second microfluidic channel.

16. The method of claim 12, wherein the gel precursor comprises agarose.

17. The method of claim 12, wherein the first fluid and the second fluid are substantially miscible.

18. The method of claim 12, wherein the microfluidic droplet containing the second fluid is contained in a carrying fluid.

19. The method of claim 12, wherein the microfluidic droplet has an average diameter of less than 1 mm.

20. A method, comprising:
transporting a first fluid containing a gel precursor at at least 0.5 vol % into a microfluidic droplet containing a second fluid; and
causing the gel precursor to solidify to form a gel particle contained within the second fluid in the microfluidic droplet,
wherein the first fluid is contained within a first microfluidic channel, the microfluidic droplet is contained within a second microfluidic channel intersecting the first microfluidic channel, and transport of the first fluid into the microfluidic droplet occurs at an intersection between the first microfluidic channel and the second microfluidic channel, and
wherein the second microfluidic channel connects to the intersection via an orifice having an area of no more than 50% of the average cross-sectional dimension of the second microfluidic channel.

21. The method of claim 20, wherein the gel precursor comprises agarose.

22. The method of claim 20, wherein the first fluid and the second fluid are substantially miscible.

23. The method of claim 20, wherein the microfluidic droplet containing the second fluid is contained in a carrying fluid.

24. The method of claim 20, wherein transporting the first fluid into the microfluidic droplet comprises applying an electric field to an interface between the first fluid and the microfluidic droplet.

* * * * *